(12) United States Patent
Bhatia

(10) Patent No.: US 8,728,549 B2
(45) Date of Patent: May 20, 2014

(54) COMPOSITIONS AND METHODS FOR TREATING SKIN CONDITIONS

(76) Inventor: Tasneem Bhatia, Atlanta, GA (US)

( * ) Notice: Subject to any disclaimer, the term of this patent is extended or adjusted under 35 U.S.C. 154(b) by 32 days.

(21) Appl. No.: 13/342,926

(22) Filed: Jan. 3, 2012

(65) Prior Publication Data

US 2013/0004595 A1 Jan. 3, 2013

Related U.S. Application Data

(60) Provisional application No. 61/429,215, filed on Jan. 3, 2011.

(51) Int. Cl.
*A61K 36/00* (2006.01)

(52) U.S. Cl.
USPC ............................ 424/773; 424/776; 424/725

(58) Field of Classification Search
None
See application file for complete search history.

(56) References Cited

U.S. PATENT DOCUMENTS

| 5,798,341 A * | 8/1998 | Klingelholler ............... 514/52 |
| 2003/0072828 A1* | 4/2003 | Harrison et al. .............. 424/776 |

* cited by examiner

*Primary Examiner* — Chris R Tate
*Assistant Examiner* — Deborah Davis
(74) *Attorney, Agent, or Firm* — Meunier Carlin & Curfman LLC; Lisa C. Pavento

(57) ABSTRACT

Provided are skin treatment compositions comprising an *Oenothera biennis* oil in an amount of about 1% v/v to about 30% v/v, a vitamin B12 in an amount of about 0.07% m/v to about 1.0% m/v, and a vitamin E in an amount of about 4% m/v to about 12% m/v. Also provided are methods for treating eczema in a mammal through the application of the skin treatment compositions to an area on the mammal's skin that contains one or more signs of eczema.

8 Claims, No Drawings

COMPOSITIONS AND METHODS FOR TREATING SKIN CONDITIONS

CROSS-REFERENCE TO RELATED APPLICATIONS

This application claims the priority benefit of U.S. Provisional Patent Application No. 61/429,215 filed Jan. 3, 2011.

FIELD OF THE INVENTION

This invention relates to compositions and methods for treating skin conditions such as eczema.

BACKGROUND OF THE INVENTION

Eczema is term for a group of medical conditions that cause the skin to become inflamed or irritated. The most common type of eczema is known as atopic dermatitis, or atopic eczema. Atopic refers to a group of diseases with an often inherited tendency to develop other allergic conditions, such as asthma and hay fever. According to the National Institute of Allergy and Infectious Disease, the prevalence of atopic eczema is increasing and affects 9 to 30% of the U.S. population. It is particularly common in young children and infants. While many infants who develop the condition outgrow it by their second birthday, some people continue to experience symptoms on and off throughout life.

Other types of eczema include nummular dermatitis, seborrheic dermatitis, irritant contact dermatitis, allergic contact dermatitis, dyshidrotic dermatitis, neurodermatitis, and stasis dermatitis. Nummular dermatitis often appears after a skin injury or insect bite. The hallmark of nummular eczema is coin-shaped or oval lesions. Seborrheic dermatitis includes conditions such as cradle cap and dandruff. Contact dermatitis is of two types: irritant contact dermatitis and allergic contact dermatitis. Irritant contact dermatitis occurs when a substance damages the skin faster than the skin can repair itself. One example of irritant contact dermatitis is diaper rash. Allergic contact dermatitis can be caused by a multitude of allergens including antibiotic ointments, concrete, fragrances, metals, and plants such as poison ivy, poison oak or poison sumac. Dyshidrotic dermatitis occurs only on the palms of the hands, sides of the fingers and soles of the feet, and its cause is generally unknown. Neurodermatitis develops when nerve endings in the skin become irritated and cause a severe scratch-itch cycle. Stasis dermatitis develops in the lower legs when circulation becomes sluggish. As fluids build up, the legs swell due to inadequate circulation and a rash develops on the skin of the legs.

The goal of treatment for eczema is to relieve and prevent itching. If left untreated, eczema can lead to an infection. Products containing hydrocortisone or stronger corticosteroids are often used in the form of creams to reduce inflammation associated with eczema. Short courses of oral corticosteroids may be prescribed in severe cases. However, all corticosteroid treatments have side effects. Topical corticosteroid use can lead to thin skin, red lesions and acne, whereas oral corticosteroid use can lead to mood swings, glaucoma, weight gain, increased blood pressure, cataracts, and osteoporosis. Other eczema treatments include antihistamines, tar treatments, phototherapy, cyclosporine, and topical immunomodulators (TIMs). TIMs are skin creams that work by altering the immune system response to prevent eczema flare-ups. Two TIMs creams carry the FDA's strongest "black box" warning on their packaging to alert doctors and patients to the possible cancer risk associated with their use.

Accordingly, despite the development of various products for the treatment of eczema, there still remains a need for effective and natural compositions for the treatment of eczema that have minimal or no side effects.

SUMMARY OF THE INVENTION

The present invention answers the need for effective yet natural compositions for the treatment of eczema. These compositions comprise the natural ingredients *Oenothera biennis* oil (also known as evening primrose oil), vitamin B12, and vitamin E. In preferred embodiments, the skin treatment composition is an emulsion and comprises *Oenothera biennis* oil in an amount of about 1% v/v to about 30% v/v, vitamin B12 in an amount of about 0.07% m/v to about 1.0% m/v, and vitamin E in an amount of about 4% m/v to about 12% m/v. More preferably, the skin treatment composition comprises *Oenothera biennis* oil in an amount of about 20% v/v, vitamin B12 in an amount of about 0.5% m/v, and vitamin E in an amount of about 5.3% m/v to 10.7% m/v.

The present invention also includes methods for treating eczema in a mammal through the application of the skin treatment compositions to an area on the mammal's skin that contains one or more signs of eczema. Signs of eczema include redness, swelling, dryness and itchiness. In preferred embodiments, the skin treatment compositions described herein are applied to the area showing signs of eczema several times a day.

DETAILED DESCRIPTION OF THE INVENTION

The present invention provides natural and effective compositions and methods for treating eczema. As used herein, the term "eczema" refers to a group of skin conditions that present dry, swollen, irritated and/or itchy skin. Types of eczema to be treated with the compositions and methods of the present invention include, but are not limited to, atopic dermatitis, nummular dermatitis, seborrheic dermatitis, irritant contact dermatitis, allergic contact dermatitis, dyshidrotic dermatitis, hand dermatitis, neurodermatitis, occupational dermatitis, and stasis dermatitis.

The natural and effective eczema treatments provided herein comprise *Oenothera biennis* oil, vitamin B12 and vitamin E. *Oenothera biennis* oil is also called evening primrose oil. *Oenothera biennis* oil contains an omega-6 essential fatty acid, gamma-linolenic acid. The term "vitamin B12" includes methylcobalamin, cyanocobalamin, hydroxycobalamin, and adenosylocobalamin. In a preferred embodiment, the vitamin B12 is cyanocobalamin and a semisolid. The term "vitamin E" includes d-alpha-Tocopherol, dl-alpha-Tocopherol, d-alpha-Tocopheryl acetate, dl-alpha-Tocopheryl acetate, d-alpha-Tocopheryl acid succinate or dl-alpha-Tocopheryl acid succinate. In a preferred embodiment, the vitamin E is an alpha Tocopherol with mixed tocopherols in the form of an oil.

In one embodiment of the present invention, the skin treatment composition comprises *Oenothera biennis* oil in an amount of about 1% v/v to about 30% v/v, and vitamin B12 and vitamin E in any amount. In another embodiment, the skin treatment composition comprises vitamin B12 in an amount of about 0.07% m/v to about 1.0% m/v, and *Oenothera biennis* oil and vitamin E in any amount. In yet another embodiment, the skin treatment composition comprises vitamin E in an amount of about 4% m/v to about 12% m/v, and *Oenothera biennis* oil and vitamin B12 in any amount. In a preferred embodiment, the skin treatment composition comprises a combination of *Oenothera biennis* oil, vitamin B12, and vitamin E wherein the amounts of one or more of those components is as follows: *Oenothera biennis* oil in an amount of about 1% v/v to about 30% v/v, vitamin B12 in an amount of about 0.07% m/v to about 1.0% m/v, and vitamin E in an amount of about 4% m/v to about 12% m/v. As used herein, the term "% m/v" is equivalent to grams per milliliter multiplied by 100.

In other embodiments of present invention, the skin treatment composition comprises about 20% v/v *Oenothera biennis* oil, and vitamin B12 and vitamin E in any amount. In another embodiment, the skin treatment composition comprises about 0.5% m/v of vitamin B12, and *Oenothera biennis* oil and vitamin E in any amount. In yet another embodiment, the skin treatment composition comprises about 5.3% m/v or 10.7% m/v of vitamin E, and *Oenothera biennis* oil and vitamin B12 in any amount. In a preferred embodiment, the skin composition comprises a combination of *Oenothera biennis* oil, vitamin B12 and vitamin E wherein the amounts of one or more of those components is as follows: *Oenothera biennis* oil in an amount of about 20% v/v, vitamin B12 in an amount of about 0.5% m/v, and vitamin E in an amount of about 5.3% m/v or about 10.7% m/v.

In further embodiments, the skin treatment composition comprises *Oenothera biennis* oil in an amount of about 0.05 ml to about 1.5 ml, vitamin B12 in an amount of about 3.5 mg to about 50 mg, and vitamin E in an amount of about 267 mg to about 534 mg in an approximately 5.0 ml solution. In one embodiment, the skin treatment composition comprises *Oenothera biennis* oil in an amount of about 1.0 ml in an approximately 5.0 ml solution. In another embodiment, the skin treatment composition comprises vitamin B12 in an amount of about 25 mg in an approximately 5.0 ml solution. In another embodiment, the skin treatment composition comprises vitamin E in an amount of about 267 mg to about 534 mg in an approximately 5.0 ml solution. In a preferred embodiment, the skin treatment composition comprises *Oenothera biennis* oil in an amount of about 1.0 ml, vitamin B12 in an amount of about 25 mg, and vitamin E in an amount of about 267 mg to about 534 mg in an approximately 5 ml solution.

The skin treatment compositions of the present invention may be formulated in any of a variety of suitable forms for topical administration. Standard pharmaceutical formulation techniques known by those of skill in the art may be used to prepare these formulations. The carrier of the skin treatment composition may aid penetration of the *Oenothera biennis* oil, vitamin B12 and/or vitamin E into the skin. Such topical skin treatment compositions may be in any form including, for example, solutions, oils, creams, ointments, gels, lotions, pastes, milks, cleansers, moisturizers, sprays, aerosols, skin patches and the like. In a preferred embodiment, the skin treatment composition is in the form of a cream. A variety of carrier materials well known in the art for topical application, such as, for example, water, alcohols, *aloe vera* gel, allantoin, glycerine, vitamin A and E oils, mineral oil, propylene glycol, and the like can be used to prepare such formulations.

Topical formulations are often prepared in the form of emulsions. The term "emulsion," as used herein refers to mixtures of two or more liquids, which may be in the form of a continuous phase and a disperse phase, for example. Exemplary emulsions may be in the form of creams, lotions, ointments, gels, etc. and may include, for example, oil-in-water emulsions, water-in-oil emulsions, multiple emulsions and microemulsions. These formulations will be prepared which contain from about 0.07 to 30 w/v % or v/v % of the *Oenothera biennis* oil, vitamin B12 and/or vitamin E.

The skin treatment compositions may also be administered topically in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. A potential formulation for topical delivery of the skin treatment compositions used in the methods of the present invention utilizes liposomes such as described in U.S. Pat. No. 4,911,928 and U.S. Pat. No. 5,834,014.

The formulations described above can be used in the methods of the present invention. The present invention includes methods of treating eczema in a mammal comprising topically administering a skin treatment composition to the mammal, wherein the composition comprises *Oenothera biennis* oil in an amount of about 1% v/v to about 30% v/v, vitamin B12 in an amount of about 0.07% m/v to about 1.0% m/v, and vitamin E in an amount of about 4% m/v to about 12% m/v. The terms "treat", "treating", "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. In some instances, the terms "treat", "treating", "treatment" and grammatical variations thereof, include partially or completely reducing redness, swelling, itchiness, cracking, fissures, and/or dryness of the skin as compared with prior to treatment of the mammal or as compared with the incidence of such symptom in a general or study population.

In preferred embodiments, approximately 1.0 ml to 10.0 ml of the composition is applied to an area of the skin that contains signs of eczema. In further preferred embodiments, approximately 5.0 ml of the composition is applied to an area of the skin that contains signs of eczema. Signs of eczema include, but are not limited to, redness (erythema), swelling, dryness, fissures, cracking, and itchiness. The skin treatment compositions can be administered to an area of the skin containing signs of eczema as needed or approximately 1 to 5 times a day. Redness, dryness, swelling and/or itchiness are reduced in the mammal following application of the skin treatment compositions of the present invention.

In preferred embodiments, the methods of treating eczema in a mammal comprise topically administering a skin treatment composition having about 1% v/v to about 30% v/v of *Oenothera biennis* oil, about 0.07% m/v to about 1% m/v of vitamin B12, and about 8% m/v of vitamin E to an area of the mammal's skin containing signs of eczema. In other preferred embodiments, the methods of treating eczema in a mammal comprise topically administering a skin treatment composition having about 1% v/v to about 30% v/v of *Oenothera biennis* oil, about 0.5% m/v of vitamin B12, and about 5.3% m/v to about 10.7% m/v of vitamin E to an area of the mammal's skin containing signs of eczema. In a further preferred embodiment, the methods of treating eczema in a mammal comprise topically administering a skin treatment composition having an amount of about 20% v/v of *Oenothera biennis* oil, about 0.07% m/v to about 1% m/v of vitamin B12, and about 5.3% m/v to about 10.7% m/v of vitamin E to an area of the mammal's skin containing signs of eczema. In still further preferred embodiments, the methods of treating eczema in a mammal comprise topically administering a skin treatment composition having 20% v/v of Oenothera biennis oil, 0.5% m/v of vitamin B12, and 8% m/v of vitamin E to an area of the mammal's skin containing signs of eczema.

EXAMPLE

The compositions and methods provided herein will be further understood by reference to the following non-limiting example.

Treatment of Patients Having Eczema

Ten human patients were treated with a composition comprising 20% v/v of *Oenothera biennis* oil, about 0.5% m/v of vitamin B12, and about 8% m/v of vitamin E. Patients were treated one or more times daily (via self-administration) for two weeks to three months with the following results:

Three patients presented with severe eczema on both hands that was characterized as erythematous, scaly and having areas of fissures and cracking. Following one month of treatment with the above-described composition, all three patients had a reduction in fissures and cracking. Following an additional one month of treatment, these three patients had decreased erythema. Within three months of consistent use of the above-described composition, these three patients had minimal to no eczema on the treated hands.

Two patients presented with generalized eczema and significant pruritus. Following two weeks of treatment with the above-described composition, itching had resolved in these two patients. Signs of eczema further decrease within one month of treatment.

Five other patients had various other beneficial responses to the administration of the above-described compositions.

It is understood that the examples and embodiments described herein are for illustrative purposes only and that various modifications or changes in light thereof will be suggested to person skilled in the art and are to be included with the spirit and purview of this applications and scope of the appended claims. All publications, patents and patent applications cited herein are hereby incorporated by reference in their entirety for all purposes.

What is claimed is:

1. A method of treating eczema in a mammal comprising topically administering a composition consisting essentially of about 1% v/v to about 30% v/v of an *Oenothera biennis* oil, about 0.5% m/v of a vitamin B12, and about 5% m/v to about 11% m/v of a vitamin E to an area of the mammal's skin containing one or more signs of the eczema, and optionally, a carrier.

2. The method of claim 1, wherein the composition consists essentially of about 20% v/v of an *Oenothera biennis* oil, about 0.5% m/v of a vitamin B12, and about 8% m/v of a vitamin E, and optionally, a carrier.

3. The method of claim 1, wherein the vitamin B12 is a cyanocobalamin.

4. The method of claim 1, wherein the vitamin E comprises an alpha Tocopherol.

5. The method of claim 1, wherein the one or more signs of the eczema are selected from the group consisting of redness, swelling, dryness, fissures, cracking, and itchiness.

6. The method of claim 1, wherein the composition is an emulsion.

7. The method of claim 1, wherein the composition is administered at least once daily.

8. The method of claim 1, wherein the mammal is a human.

* * * * *